United States Patent [19]

Burgess et al.

[11] Patent Number: 6,077,864
[45] Date of Patent: Jun. 20, 2000

[54] CYCLIC SULFONE DERIVATIVES

[75] Inventors: Laurence Edward Burgess, Boulder; James Patrick Rizzi, Niwot, both of Colo.

[73] Assignee: Pfizer Inc., New York, N.Y.

[21] Appl. No.: 09/331,275

[22] PCT Filed: Dec. 18, 1997

[86] PCT No.: PCT/IB97/01582

§ 371 Date: Jun. 17, 1999

§ 102(e) Date: Jun. 17, 1999

[87] PCT Pub. No.: WO98/30566

PCT Pub. Date: Jul. 16, 1998

Related U.S. Application Data

[60] Provisional application No. 60/034,535, Jan. 6, 1997.

[51] Int. Cl.[7] .......................... A01N 43/08; A61K 31/34; C07D 307/00; C07D 307/93
[52] U.S. Cl. .......................... 514/468; 546/146; 546/172; 546/196; 546/256; 548/159; 548/204; 548/214; 548/217; 548/235; 548/247; 548/253; 548/305.1; 548/311.4; 548/364.4; 548/464; 548/525; 549/58; 549/60; 549/459; 549/463
[58] Field of Search ................ 549/459, 58, 60, 549/463; 544/61, 153, 277, 336, 361; 546/146, 172, 196, 256, 87; 548/159, 204, 214, 217, 235, 247, 253, 305.1, 311.4, 364.4, 464, 525; 514/468, 228.2, 228.8, 255, 266, 307, 314, 320, 337–365, 367–372, 374, 375, 378, 382, 394, 397, 406, 414, 422, 443, 444, 469, 470

[56] References Cited

U.S. PATENT DOCUMENTS 3,268,539 8/1966 Levy ........................................ 260/294

FOREIGN PATENT DOCUMENTS

| 0453960 | 10/1991 | European Pat. Off. . |
| 0453960A1 | 10/1991 | European Pat. Off. ...... C07D 493/08 |
| 0606046A1 | 7/1994 | European Pat. Off. ...... C07D 213/42 |
| 0780386A1 | 6/1997 | European Pat. Off. ...... C07D 309/08 |

OTHER PUBLICATIONS

Marvin Stolberg et al. .."Vicinally Substituted Hydroxamic Acids" May 20, 1957.

*Primary Examiner*—Mukund J. Shah
*Assistant Examiner*—T. Benjamin Schroeder
*Attorney, Agent, or Firm*—Peter C. Richardson; Paul H. Ginsburg; Jolene W. Appleman

[57] ABSTRACT

A compound of the formula

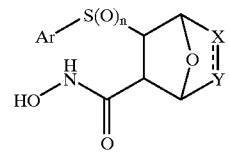

I wherein n, X, Y and Ar are as defined herein, useful in the treatment of a condition selected from the group consisting of arthritis, cancer, tissue ulceration, macular degeneration, restenosis, periodontal disease, epidermolysis bullosa, scleritis, and other diseases characterized by matrix metalloproteinase activity, AIDS, sepsis, septic shock and other diseases involving the production of TNF. In addition, the compounds of the present invention may be used in combination therapy with standard non-steroidal anti-inflammatory drugs (NSAID'S) and analgesics, and in combination with cytotoxic drugs such as adriamycin, daunomycin, cis-platinum, etoposide, taxol, taxotere and other alkaloids, such as vincristine, in the treatment of cancer.

8 Claims, No Drawings

CYCLIC SULFONE DERIVATIVES

CROSS-REFERENCE TO RELATED APPLICATIONS

This application is a national stage entry under 35 U.S.C. §371 of PCT/IB97/01582, filed Dec. 18, 1997 which claims the benefit of U.S. Provisional Application No. 06/034,535 filed, Jan. 6, 1997.

BACKGROUND OF THE INVENTION

The present invention relates to cyclic sulfone derivatives which are inhibitors a matrix metalloproteinases or the production of tumor necrosis factor (TNF) and as such are useful in the treatment of a condition selected from the group consisting of arthritis, cancer, tissue ulceration, restenosis, periodontal disease, epidermolysis bullosa, scleritis and other diseases characterized by matrix metalloproteinase activity, AIDs, sepsis, septic shock and other diseases involving the production of TNF. In addition, the compounds of the present invention may be used in combination therapy with standard non-steroidal anti-inflammatory drugs (hereinafter NSAID'S) and analgesics for the treatment of arthritis, and in combination with cytotoxic drugs such as adriamycin, daunomycin, cis-platinum, etoposide, taxol, taxotere and alkaloids, such as vincristine, in the treatment of cancer.

This invention also relates to a method of using such compounds in the treatment of the above diseases in mammals, especially humans, and to pharmaceutical compositions useful therefor.

There are a number of enzymes which effect the breakdown of structural proteins and which are structurally related metalloproteases. Matrix-degrading metalloproteinases, such as gelatinase, stromelysin and collagenase, are involved in tissue matrix degradation (e.g. collagen collapse) and have been implicated in many pathological conditions involving abnormal connective tissue and basement membrane matrix metabolism, such as arthritis (e.g. osteoarthritis and rheumatoid arthritis), tissue ulceration (e.g. corneal, epidermal and gastric ulceration), abnormal wound healing, periodontal disease, bone disease (e.g. Paget's disease and osteoporosis), tumor metastasis or invasion, as well as HIV-infection (*J. Leuk. Biol.*, 52 (2): 244–248, 1992).

Tumor necrosis factor is recognized to be involved in many infectious and auto-immune diseases (W. Fiers, *FEBS Letters*, 1991, 285, 199). Furthermore, it has been shown that TNF is the prime mediator of the inflammatory response seen in sepsis and septic shock (C. E. Spooner et al., *Clinical Immunology and Immunopathology*, 1992, 62 S11).

SUMMARY OF THE INVENTION

The present invention relates to a compound of the formula

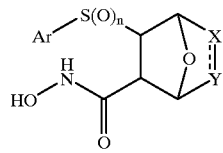

I or pharmaceutically acceptable salt thereof, wherein the broken line represents an optional double bond;

n is 0, 1 or 2;

X and Y are each independently $CR^1$ wherein $R^1$ is hydrogen, $(C_1-C_6)$alkyl optionally substituted by $(C_1-C_6)$alkylamino, $(C_1-C_6)$alkylthio, $(C_1-C_6)$alkoxy, trifluoromethyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$heteroarylthio, $(C_5-C_9)$heteroaryloxy, $(C_6-C_{10})$aryl$(C_6-C_{10})$aryl, $(C_3-C_6)$cycloalkyl, hydroxy$(C_1-C_6)$alkyl, $(C_1-C_6)$alkyl(hydroxymethylene), piperazinyl, $(C_6-C_{10})$aryl$(C_1-C_6)$alkoxy, $(C_5-C_9)$heteroaryl$(C_1-C_6)$alkoxy, $(C_1-C_6)$acylamino, $(C_1-C_6)$acylthio, $(C_1-C_6)$acyloxy, $(C_1-C_6)$alkylsulfinyl, $C_6-C_{10}$)arylsulfinyl, $(C_1-C_6)$alkylsulfonyl, $(C_6-C_{10})$arylsulfonyl, amino, $C_1-C_6$)alkylamino or $((C_1-C_6)$alkyl$)_2$amino; trifluoromethyl, $(C_1-C_6)$alkyl (difluoromethylene), $(C_1C_3)$alkyl(difluoromethylene) $(C_1-C_3)$alkyl, $(C_6-C_{10})$aryl, $(C_5-C_9)$heteroaryl, $(C_3-C_6)$cycloalkyl, $(C_1-C_6)$alkyl-(hydroxymethylene), $R^3(C_1-C_6)$alkyl wherein $R^3$ is $(C_1-C_6)$acylpiperazino, $(C_6-C_{10})$arylpiperazino, $(C_5-C_9)$heteroarylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino, pyrrolidino, piperidyl, $(C_1-C_6)$alkylpiperidyl, $(C_6-C_{10})$arylpiperidyl, $(C_5-C_9)$heteroarylpiperidyl, $C_1-C_6$)alkylpiperidyl$(C_1-C_6)$alkyl, $(C_6-C_{10})$arylpiperidyl$(C_1-C_6)$alkyl, $(C_5-C_9)$heteroarylpiperidyl$(C_1-C_6)$alkyl or $(C_1-C_6)$acylpiperidyl;

or a group of the formula

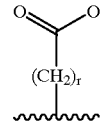

wherein r is 0 to 6;

D is hydroxy, $(C_1-C_6)$alkoxy, piperidyl, $(C_1-C_6)$alkylpiperidyl, $(C_6-C_{10})$arylpiperidyl, $(C_5-C_9)$heteroarylpiperidyl, $(C_1-C_6)$acylpiperidyl or $NR^4R^5$ wherein $R^4$ and $R^5$ are each independently selected from the group consisting of hydrogen, $(C_1-C_6)$alkyl optionally substituted by $(C_1-C_6)$alkylpiperidyl,$(C_6-C_{10})$arylpiperidyl, $(C_5-C_9)$heteroarylpiperidyl, $(C_6-C_{10})$aryl,$(C_5-C_9)$heteroaryl,$(C_6-C_{10})$aryl$(C_6-C_{10})$aryl or $(C_3-C_6)$cycloalkyl; $(C_6-C_{10})$aryl, $(C_5-C_9)$heteroaryl, $(C_6-C_{10})$aryl$(C_6-C_{10})$aryl, $(C_3-C_6)$cycloalkyl, $R^6(C_2-C_6)$alkyl, $(C_1-C_5)$alkyl $(CHR^6)(C_1-C_6)$alkyl wherein $R^6$ is hydroxy, $(C_1-C_6)$acyloxy, $(C_1-C_6)$alkoxy, piperazino, $(C_1-C_6)$acylamino, $(C_1-C_6)$alkylthio, $(C_6-C_{10})$arylthio, $(C_1-C_6)$alkylsulfinyl, $(C_6-C_{10})$arylsulfinyl,$(C_1-C_6)$alkylsulfoxyl, $(C_6-C_{10})$arylsulfoxyl, amino, $(C_1-C_6)$alkylamino, $((C_1-C_6)$alkyl$)_2$amino, $(C_1-C_6)$acylpiperazino, $(C_1-C_6)$alkylpiperazino, $(C_6-C_{10})$aryl$(C_1-C_6)$alkylpiperazino,$(C_5-C_9)$heteroaryl $(C_1-C_6)$alkylpiperazino, morpholino, thiomorpholino, piperidino or pyrrolidino; $R^7(C_1-C_6)$alkyl, $(C_1-C_5)$alkyl$(CHR^7)$ $(C_1-C_6)$alkyl wherein $R^7$ is piperidyl or $(C_1-C_6)$ alkylpiperidyl; and $CH(R^8)COR^9$ wherein $R^8$ is hydrogen, $(C_1-C_6)$alkyl, $(C_6-C_{10})$aryl$(C_1-C_6)$alkyl, $(C_5-C_9)$ heteroaryl$(C_1-C_6)$alkyl, $(C_1-C_6)$alkylthio$(C_1-C_6)$alkyl, $(C_6-C_{10})$arylthio$(C_1-C_6)$alkyl, $(C_1-C_6)$alkylsulfinyl $(C_1-C_6)$alkyl, $(C_6-C_{10})$arylsulfinyl$(C_1-C_6)$alkyl, $(C_1-C_6)$ alkylsulfonyl$(C_1-C_6)$alkyl, $(C_6-C_{10})$arylsulfonyl$(C_1-C_6)$ alkyl, hydroxy$(C_1-C_6)$alkyl, amino$(C_1-C_6)$alkyl, $(C_1-C_6)$ alkylamino$(C_1-C_6)$alkyl, $((C_1-C_6)$alkylamino$)_2(C_1-C_6)$ alkyl, $R^{10}R^{11}NCO(C_1-C_6)$alkyl or $R^{10}OCO(C_1-C_6)$alkyl wherein $R^{10}$ and $R^{11}$ are each independently selected from the group consisting of hydrogen, $(C_1-C_6)$alkyl, $(C_6-C_{10})$ aryl($C_1$–$C_6$)alkyl and ($C_5$–$C_9$)heteroaryl($C_1$–$C_6$)alkyl; and $R^9$ is $R^{12}O$ or $R^{12}R^{13}N$ wherein $R^{12}$ and $R^{13}$ are each independently selected from the group consisting of hydrogen, ($C_1$–$C_6$)alkyl, ($C_6$–$C_{10}$)aryl($C_1$–$C_6$)alkyl and ($C_5$–$C_9$)heteroaryl($C_1$–$C_6$)alkyl; and Ar is ($C_1$–$C_6$)alkyl, ($C_6$–$C_{10}$)aryl, ($C_6$–$C_{10}$)aryloxy ($C_6$–$C_{10}$)aryl, ($C_6$–$C_{10}$)aryl($C_6$–$C_{10}$)aryl, ($C_6$–$C_{10}$)aryl ($C_6$–$C_{10}$)aryl($C_1$–$C_6$)alkyl, ($C_6$–$C_{10}$)aryloxy($C_5$–$C_9$) heteroaryl, ($C_5$–$C_9$)heteroaryl, ($C_1$–$C_6$)alkyl($C_6$–$C_{10}$)aryl, ($C_1$–$C_6$)alkoxy($C_6$–$C_{10}$)aryl, ($C_6$–$C_{10}$)aryl($C_1$–$C_6$)alkoxy ($C_6$–$C_{10}$)aryl, ($C_6$–$C_{10}$)aryl($C_1$–$C_6$)alkoxy($C_1$–$C_6$)alkyl, ($C_5$–$C_9$)heteroaryloxy($C_6$–$C_{10}$)aryl, ($C_1$–$C_6$)alkyl($C_5$–$C_9$) heteroaryl, ($C_1$–$C_6$)alkoxy($C_5$–$C_9$)heteroaryl, ($C_6$–$C_{10}$)aryl ($C_1$–$C_6$)alkoxy($C_5$–$C_9$)heteroaryl, ($C_5$–$C_9$)heteroaryloxy ($C_5$–$C_9$)heteroaryl, ($C_6$–$C_{10}$)aryloxy($C_1$–$C_6$)alkyl, ($C_5$–$C_9$) heteroaryloxy($C_1$–$C_6$)alkyl, ($C_1$–$C_6$)alkyl($C_6$–$C_{10}$)aryloxy ($C_6$–$C_{10}$)aryl, ($C_1$–$C_6$)alkyl($C_5$–$C_9$)heteroaryloxy($C_6$–$C_{10}$) aryl, ($C_1$–$C_6$)alkyl($C_6$–$C_{10}$)aryloxy($C_5$–$C_9$)heteroaryl, ($C_1$–$C_6$)alkoxy($C_6$–$C_{10}$)aryloxy($C_6$–$C_{10}$)aryl,($C_1$–$C_6$) alkoxy($C_5$–$C_9$)heteroaryloxy($C_6$–$C_{10}$)aryl or ($C_1$–$C_6$) alkoxy($C_6$–$C_{10}$)aryloxy($C_5$–$C_9$)heteroaryl wherein each aryl group is optionally substituted by fluoro, chloro, bromo, ($C_1$–$C_6$)alkyl, ($C_1$–$C_6$)alkoxy or perfluoro($C_1$–$C_3$)alkyl.

The term "alkyl", as used herein, unless otherwise indicated, includes saturated monovalent hydrocarbon radicals having straight, branched or cyclic moieties or combinations thereof.

The term "alkoxy", as used herein, includes alkyl-O groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents independently selected from the group consisting of fluoro, chloro, cyano, nitro, trifluoromethyl, ($C_1$–$C_6$)alkoxy, ($C_6$–$C_{10}$)aryloxy, trifluoromethoxy, difluoromethoxy and ($C_1$–$C_6$)alkyl.

The term "heteroaryl", as used herein, unless otherwise indicated, includes an organic radical derived from an aromatic heterocyclic compound by removal of one hydrogen, such as pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 2 substituents independently selected from the group consisting of fluoro, chloro, trifluoromethyl, ($C_1$–$C_6$)alkoxy, ($C_6$–$C_{10}$)aryloxy, trifluoromethoxy, difluoromethoxy and ($C_1$–$C_6$)alkyl.

The term "acyl", as used herein, unless otherwise indicated, includes a radical of the general formula RCO wherein R is alkyl, alkoxy, aryl, arylalkyl or arylalkyloxy and ther terms "alkyl" or "aryl" are as defined above.

The term "acyloxy", as used herein, includes acyl-O groups wherein "acyl" is defined above.

Preferred compounds of formula I include those wherein n is 2.

Other preferred compounds of formula I include those wherein X and Y are both $CR^1$ wherein $R^1$ is hydrogen.

Other preferred compounds of formula I include those wherein Ar is ($C_1$–$C_6$)alkoxy($C_6$–$C_{10}$)aryl($C_6$–$C_{10}$)aryl ($C_1$–$C_6$)alkoxy($C_6$–$C_{10}$)aryl,4-fluorophenoxy($C_6$–$C_{10}$)aryl, 4-fluorobenzyloxy($C_6$–$C_{10}$)aryl or ($C_1$–$C_6$)alkyl($C_6$–$C_{10}$) aryloxy($C_6$–$C_{10}$)aryl.

Most preferred compounds of formula I include those wherein n is 2, X and Y are both $CR^1$ wherein $R^1$ is hydrogen and Ar is ($C_1$–$C_6$)alkoxy($C_6$–$C_{10}$)aryl, ($C_6$–$C_{10}$)aryl($C_1$–$C_6$) alkoxy($C_6$–$C_{10}$)aryl, 4-fluorophenoxy($C_6$–$C_{10}$)aryl, 4-fluorobenzyloxy($C_6$–$C_{10}$)aryl or ($C_1$–$C_6$)alkyl($C_6$–$C_{10}$) aryloxy($C_6$–$C_{10}$)aryl.

The present invention also relates to a pharmaceutical composition for (a) the treatment of a condition selected from the group consisting of arthritis, cancer, synergy with cytotoxic anticancer agents, tissue ulceration, macular degeneration, restenosis, periodontal disease, epidermolysis bullosa, scleritis, in combination with standard NSAID's and analgesics and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of formula I or a pharmaceutically acceptable salt thereof effective in such treatments and a pharmaceutically acceptable carrier.

The present invention also relates to a method for the inhibition of (a) matrix metalloproteinases or (b) the production of tumor necrosis factor (TNF) in a mammal, including a human, comprising administering to said mammal an effective amount of a compound of formula I or a pharmaceutically acceptable salt thereof.

The present invention also relates to a method for treating a condition selected from the group consisting of arthritis, cancer, tissue ulceration, macular degeneration, restenosis, periodontal disease, epidermolysis bullosa, scleritis, compounds of formula I may be used in combination with standard NSAID's and analgesics and in combination with cytotoxic anticancer agents, and other diseases characterized by matrix metalloproteinase activity, AIDS, sepsis, septic shock and other diseases involving the production of tumor necrosis factor (TNF) in a mammal, including a human, comprising administering to said mammal an amount of a compound of formula I or a pharmaceutically acceptable salt thereof effective in treating such a condition.

DETAILED DESCRIPTION OF THE INVENTION

The following reaction Schemes illustrate the preparation of the compounds of the present invention. Unless otherwise indicated X, Y and Ar in the reaction Schemes and the discussion that follow are defined as above.

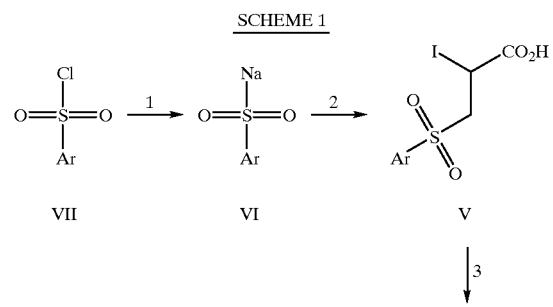

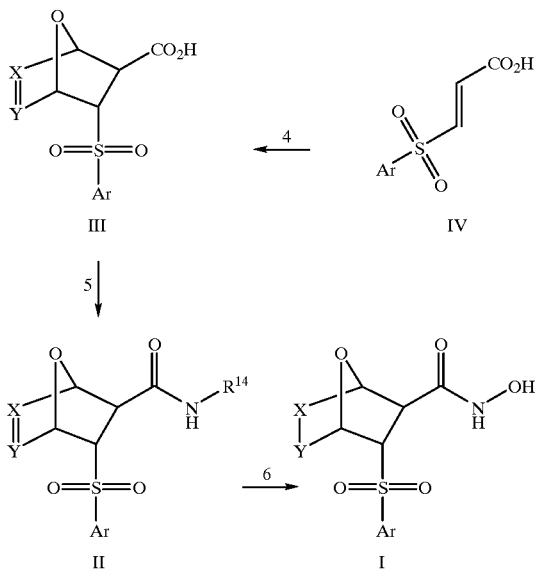

In reaction 1 Scheme 1, the aryl sulfonyl chloride compound formula VII is converted to the corresponding sodium aryl sulfonate compound of formula VI by reacting VII with sodium iodine in the presence of a polar aprotic solvent, such as acetone, under inert atmosphere. The reaction mixture is stirred, at room temperature, for a time period between about 12 hours to about 18 hours, preferably about 15 hours.

In reaction 2 of Scheme 1, the compound of formula VI is converted to the corresponding 2-iodo-3-(aryl) sulfonyl propionic acid compound of formula V by reacting VI with acrylic acid and iodine in the presence of a polar aprotic solvent, such as methylene chloride. The reaction mixture is stirred under inert atmosphere, at room temperature, for a time period between about 12 hours to about 3.5 days, preferably about 3 days.

In reaction 3 of Scheme 1, the compound of formula V is converted to the corresponding (E)-3-(aryl)sulfonyl-prop-2-enoic acid compound of formula IV by treating V with a base, such as triethylamine, in a polar aprotic solvent, such as methylene chloride, under inert atmosphere. The reaction is stirred, at room temperature, for a time period between about 10 hours to about 24 hours, preferably about 12 hours.

In reaction 4 of Scheme 1, the compound of formula IV is converted to the corresponding carboxylic acid compound of formula III by heating IV with an excess amount of a compound of the formula

to reflux in the presence of a polar aprotic solvent, such as toluene, for a time period between about 24 hours to about 56 hours, preferably about 48 hours.

In reaction 5 of Scheme 1, the compound of formula III is converted to the corresponding N-($R^{14}$)-carboxamide compound of formula II, wherein $R^{14}$ is O-substituted oxy, such as O-benzylhydroxy of trimethylsilyl ethylhydroxy by reacting III with an activating agent, such as dimethylaminopyridine/dicyclohexylcarbodiimide, and an O-substituted hydroxylamine, such as benzylhydroxylamine hydrochloride or O-trimethyl-silylethylhydroxylamine, in the presence of a polar aprotic solvent, such as methylene chloride, under inert atmosphere. The reaction mixture is stirred, at room temperature, for a time period between about 15 hours to about 25 hours, preferably about 20 hours.

In reaction 6 of Scheme 1, the compound of formula II is converted to the corresponding hydroxamic acid compound of formula I by (1) treating II with hydrogen in the presence of a catalyst, such as 5% palladium on barium sulfate, and a polar aprotic solvent, such as methanol, (2) treating II with trifluoroacetic acid or boron trifluoride diethyl etherate in a polar aprotic solvent, such as methylene chloride, or (3) treating II with tetrabutyl ammonium fluoride in a polar aprotic solution, such as tetrahydrofuran. The reaction mixture is stirred for a time period between about 2 hours to about 4 hours, preferably about 3 hours.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium slats, such as ammonium, trimethyl-ammonium, diethylammonium, and tris-(hydroxymethyl)-methylammonium slats.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The ability of the compounds of formula I or their pharmaceutically acceptable salts (hereinafter also referred to as the compounds of the present invention) to inhibit matrix metalloproteinases or the production of tumor necrosis factor (TNF) and, consequently, demonstrate their effectiveness for treating diseases characterized by matrix metalloproteinase or the production of tumor necrosis factor is shown by the following in vitro assay tests.

Biological Assay

Inhibition of Human Collagenase (MMP-1)

Human recombinant collagenase is activated with trypsin using the following ratio: 10 μg trypsin per 100 μg of collagenase. The trypsin and collagenase are incubated at room temperature for 10 minutes then a five fold excess (50 μg/10 μg trypsin) of soybean trypsin inhibitor is added.

10 mM stock solutions of inhibitors are made up in dimethyl sulfoxide and then diluted using the following Scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1–D6 and blanks (no enzyme, no inhibitors) are set in wells D7–D12.

Collagenase is diluted to 400 ng/ml and 25 μl is then added to appropriate wells of the microfluor plate. Final concentration of collagenase in the assay is 100 ng/ml.

Substrate (DNP-Pro-Cha-Gly-Cys(Me)-His-Ala-Lys (NMA)-$NH_2$) is made as a 5 mM stock in dimethyl sulfoxide and then diluted to 20 μM in assay buffer. The assay is initiated by the addition of 50 μl substrate per well of the microfluor plate to give a final concentration of 10 μM.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration vs % control (inhibitor fluorescence divided by fluorescence of collagenase alone×100). $IC_{50}$'s are determined from the concentration of inhibitor that gives a signal that is 50% of the control.

If $IC_{50}$s are reported to be <0.03 µM then the inhibitors are assayed at concentrations of 0.3 µM, 0.03 µM, 0.03 µM and 0.003 µM.

Inhibition of Gelatinase (MMP-2)

Inhibition of gelatinase activity is assayed using the Dnp-Pro-Cha-Gly-Cys(Me)-His-Ala-Lys(NMA)-$NH_2$ substrate (10 µM) under the same conditions as inhibition of human collagenase (MMP-1).

72kD gelatinase is activated with 1 mM APMA (p-aminophenyl mercuric acetate) for 15 hours at 4° C. and is diluted to give a final concentration in the assay of 100 mg/ml. Inhibitors are diluted as for inhibition of human collagenase (MMP-1) to give final concentrations in the assay of 30 M, 3 µM, 0.3 µM and 0.03 µM. Each concentration is done in triplicate.

Fluorescence readings (360 nm excitation, 460 emission) are taken at time zero and the at 20 minutes intervals for 4 hours.

$IC_{50}$'s are determined as per inhibition of human collagenase (MMP-1). If $IC_{50}$'s are reported to be less than 0.03 µM, then the inhibitors are assayed at final concentrations of 0.3 µM, 0.03 µM, 0.003 µM and 0.003 µM.

Inhibition of Stromelysin Activity (MMP-3)

Inhibition of stomelysin activity is based on a modified spectrophotometric assay described by Weingarten and Feder (Weingarten, H. and Feder, J., Spectrophotometric Assay for Vertebrate Collagenase, Anal. Biochem. 147, 437–440 (1985)). Hydrolysis of the thio peptolide substrate [Ac-Pro-Leu-Gly-SCH[$CH_2CH(CH_3)_2$]CO-Leu-Gly-$OC_2H_5$] yields a mercaptan fragment that can be monitored in the presence of Ellman's reagent.

Human recombinant prostromelysin is activated with trypsin using a ratio of 1 µl of a 10 mg/ml trypsin stock per 26 µg of stromelysin. The trypsin and stromelysin are incubated at 37° C. for 15 minutes followed by 10 µl of 10 mg/ml soybean trypsin inhibitor for 10 minutes at 37° C. for 10 minutes at 37° C. to quench trypsin activity.

Assays are conducted in a total volume of 250 µl of assay buffer (200 mM sodium chloride, 50 mM MES, and 10 mM calcium chloride, pH 6.0) in 96-well microliter plates. Activated stromelysin is diluted in assay buffer to 25 µg/ml. Ellman's reagent (3-Carboxy-4-nitrophenyl disulfide) is made as a 1M stock in dimethyl formamide and diluted to 5 mM in assay buffer with 50 µl per well yielding at 1 mM final concentration.

10 mM stock solutions of inhibitors are made in dimethyl sulfoxide and diluted serially in assay buffer such that addition of 50 µL to the appropriate well yields final concentrations of 3 µM, 0.3 µM, 0.003 µM, and 0.0003 µM. All conditions are completed in triplicate.

A 300 mM dimethyl sulfoxide stock solution of the peptide substate is diluted to 15 mM in assay buffer and the assay is initiated by addition of 50 µl to each well to give a final concentration of 3 mM substrate. Blanks consist of the peptide substrate and Ellman's reagent without the enzyme. Product formation was monitored at 405 nm with a Molecular Devices UVmax plate reader.

$IC_{50}$ values were determined in the same manner as for collagenase.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 µM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 µM, 3 µM, 0.3 µM, and 0.03 µM.

Substrate (Dnp-Pro-Cha-Gly-Cys(Me)-His-Ala-Lys (NMA)-$NH_2$) is prepared as for inhibition of human collagenase (MMP-1) and 50 µl is added to each well to give a final assay concentration of 10 mM. Fluorescence readings (360 nM excitation; 450 emission) are taken at time 0 and every 5 minutes for 1 hour.

Positive controls consist of enzyme and substrate with no inhibitor and blanks consist of substate only.

$IC_{50}$'s are determined as per inhibition of human collagenase (MMP-1). If $IC_{50}$'s are reported to be less than 0.03 µM, inhibitors are then assayed at final concentrations of 0.3 µM, 0.03 µM, 0.003 µM and 0.0003 µM.

Inhibition of TNF Production

The ability of the compounds or the pharmaceutically acceptable salts thereof to inhibit the production TNF and, consequently, demonstrate their effectiveness for treating diseases involving the production of TNF is shown by the following in vitro assay:

Human mononuclear cells were isolated from anti-coagulated human blood using a one-step Ficoli-hypaque separation technique. (2) The mononuclear cells were washed three times in Hanks balanced salt solution (HBSS) with divalent cations and resuspended to a density of $2 \times 10^6$/ml in HBSS containing 1% BSA. Differential counts determined using the Abbott Cell Dyn 3500 analyzer indicated that monocytes ranged from 17 to 24% of the total cells in these preparations.

180 µof the cell suspension was aliquoted into flate bottom 95 well plates (Costar). Additions of compounds and LPS (100 ng/ml final concentration) gave a final volume of 100 µl. All conditions were performed in triplicate. After a four hour incubation at 37° C. in an humidified $CO_2$ incubator, plates were removed and centrifuged (10 minutes at approximately 250×g) and the supernatants removed and assayed for TNFα using the R&D ELISA Kit.

For administration to humans for the inhibition of matrix metalloproteinases or the production of tumor necrosis factor, a variety of conventional routes may be used including orally, parenterally and topically, In general, the active compound will be administered orally or parentally at dosages between about 0.1 and 25 mg/kg body weight of the subject to be treated per day, preferably from about 0.3 and 5 mg/kg. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

Additionally, it is possible to administer the compounds of the present invention topically, e.g., when treating inflammatory conditions of the skin and this may be done by way of creams, jellies, gels, pastes, and ointments, in accordance with standard pharmaceutical practice.

The present invention is illustrated by the following examples, but is not limited to the details thereof.

EXAMPLE 1

3-(4-Methoxyphenylsufonyl-7-oxabicyclo[2.2.1] heptane-2-carboxylic acid hydroxyamide (a) Sodiumiodide (21.76 grams, 145.2 mmol) and 4-methoxybenzenesulfonyl chloride (10.0 grams, 48.39 mmol) were combined in dry acetone (dried over $MgSO_4$ and filtered) (200 ml) and stirred at room temperature overnight. Collected fine white solids via suction filtration. Dried on high vacuum giving 9.11 grams of sodium 4-methoxybenzenesulfinate as a pale yellow fine powder (97% yield).

(b) Added water (0.85 grams, 0.85 ml) followed by the acrylic acid (3.42 grams, 3.25 ml), then $I_2$ (12.04 grams, 47.41 mmol) to a slurry of sodium (4-methoxybenzenesulfinate (9.11 grams, 46.94 mmol) in methylene chloride (150 ml). Added more methylene chloride (100 ml) so slurry could stir. Stirred at room temperature for weekend. Washed reaction solution with 1N $Na_2S_2O_3$ (aq) (3×150 ml) until organic layer was colorless. Washed organic layer with brine. Dried ($MgSO_4$), filtered and concentrated in vacuo, to give 4.23 grams (25%) of crude 2-iodo-3-(4-methoxyphenylsulfonyl)propionic acid.

(c) 2-Iodo-3-(4-methoxyphenylsulfonyl)propionic acid (4.23 grams, 11.43 mmol) and $Et_3N$ (3.22 ml, 2.34 grams, 23.09 mmol) were combined in methylene chloride (150 ml) and stirred overnight at room temperature. The reaction mixture was diluted with 1N hydrochloric acid(aq) (100 ml). The separated aqueous layer was extracted with $Et_2O$ (2×). The dried ($MgSO_4$) combined organics were then filtered and concentrated in vacuo to give 2.58 grams of crude product. This was filtered, the filtrate concentrated and the residue taken up in methanol, filtered and the filtrate concentrated to give 1.87 grams of crude product. This was taken up in hot methylene chloride. Fine crystals crashed out. Decanted filtrate. Washed crystals methylene chloride (2×1 ml) (decanted washings). Dried crystals on high vac to give 0.396 grams of 3-(4-Methoxyphenylsulfonyl)propenoic acid as a pale yellow solid (m.p.: 123°–128.5° C.). The filtrate was concentrated to give 1.42 grams of yellow solid which was flash chromatographed (60% EtOAc/hexane/2%/ HOAc/0.5% methanol) to give 1.42 grams of 3-(4-Methoxyphenylsulfonyl)propenoic acid. A second chromatography (40% EtOAc/hexane/2%/HOAc/0.5% methanol) gave 0.568 grams of pure 3-(4-Methoxyphenylsulfonyl) propenoic acid.

(d) 3-(4-Methoxyphenylsulfonyl)propenoic acid (200 mgs), excess furan (5.0 ml), and dry toluene (5.0 ml) were combined and warmed to 55° C. (at which time starting material went into solution) for overnight. The cooled reaction was concentrated in vacuo to a tan solid which was a mixture of starting material and product. The material was taken up in toluene (5 ml) and furan (10 ml) and heated to 69° C. overnight. The cooled reaction mixture was concentrated in vacuo to give 251 mgs of crude 3-(4-Methoxyphenylsulfonyl)-7-oxabicyclo[2.2.1]hept-5-ene-2-carboxylic acid as a dark tan solid.

(e) Added the O-benzylhydroxylamine·hydrochloric acid (0.387 grams, 2.43 mmol) to a stirred solution of 3-(4-methoxy-phenylsulfonyl-7-oxabicyclo[2.2.1]hept-5-ene-2-carboxylic acid in methylene chloride (5 ml). Added 4-dimethylaminopyridine (0.306 grams, 2.51 mmol) and stirred approximately one-half hour (until solids dissolved), then added the 1,3-dicyclohexylcarbodiimide (0.250 grams, 1.21 mmol) and stirred at room temperature overnight. The reaction was filtered through a pad of Celite and the filtrate concentrated in vacuo to give 1.06 grams of 3-(4-Methoxyphenylsulfonyl-7-oxabicyclo[2.2.1]heptane-2-carboxylic acid benzyloxyamide. Took this up in methanol and decanted filtrate from fine needle crystals. Concentration of filtrate gave 0.82 grams of 3-(4-Methoxyphenylsulfonyl-7-oxabicyclo[2.2.1]heptane-2-carboxylic acid benzyloxyamide.

(f) Added 5% palladium/barium sulfate (0.80 grams) to crude (3-(4-methoxyphenylsulfonyl-7-oxa-bicyclo[2.2.1]hept-5-ene-2-carboxylic acid benzyloxy amide (0.82 grams) in 30 ml methanol and hydrogenated at 45 psi at room temperature on a Parr Shaker for 4 hours. Filtered the reaction through a pad of Celite and concentrated the filtrate in vacuo. $^1$H-NMR of the residue shows only the double bond has been removed. The residue was flash chromatographed (50% EtOAc/hexane) to give 0.126 grams of intermediate. To this was added 5% palladium/barium sulfate (0.126 grams) in methanol (30 ml) and hydrogenation was continued on a Parr Shaker at 45 psi at room temperature for 1 ¾ hours. Filtered the reaction through a pad of Celite and concentrated the filtrate to give 0.101 grams of crude 3-(4-Methoxyphenylsulfonyl-7-oxabicyclo[2.2.1]heptane-2-carboxylic acid hydroxyamide. Flash chromatographed (70/30/8/1) (EtOAc/hexane/methanol/HOAc) to give 77.1 mg of 3-(4-Methoxyphenylsulfonyl-7-oxabicyclo[2.2.1]heptane-2-carboxylicacidhydroxyamide. $^1$H-NMR (CD$_3$OD) δ 1.6 (2H, m), 1.8 (2H, m), 3.11 (1H, t), 3.82 (1H, d), 3.88 (3H, s), 4.63 (1H, t), 4.91 (1H, d), 7.12 (2H, d), 7.80 (2H, d); HRMS M$^{30}$ +H$^+$, Calc'd: 3.28.0855, Found 328.0872.

EXAMPLE 2

3-(4-Phenoxyphenylsulfonyl-7-oxabicyclo[2.2.1]heptane-2-carboxylic acid hydroxyamide (a) 3-(4-Phenoxyphenylsulfonyl)propenoic acid prepared from 4-phenoxyphenylsulfonyl chloride and acrylic acid as described in Example 1 steps A and B was flash chromatographed (60/40/1.5/0.5—EtOAc/hexane/HOAc/methanol) to give 1.12 grams of product as an off-white solid. This was crystallized from EtOAc/hexane (3:1) to give 0.61 grams of pure product as fine white crystals.

(b) To 3(4-phenoxyphenylsulfonyl)propenoic acid (250 mgs, 0.82 mmol) in toluene (5.0 ml) (starting material insoluble in toluene at room temperature) was added furan (10 ml) and the mixture heated to gentle reflux approximately 70° C. After approximately one-half hour the reaction mixture was a solution. After 18 hours of reflux TLC of the milky white solution shows starting material to be consumed. The reaction mixture was cooled and the white precipitate collected via suction filtration and washed with toluene (2×1 ml). Dissolved solids in hot methanol and concentrated in vacuo to give 0.267 grams of 2-(4-Phenoxyphenylsulfonyl-7-oxabicyclo[2.2.1]hept-5-ene-2-carboxylic acid as a white crystalline solid.

(c) 3-(4-Phenoxyphenylsulfonyl-7-oxabicyclo[2.2.1]hept-5-ene-2-carboxylic acid (0.243 grams, 0.65 mmol) was hydrogenated on a Parr Shaker over 5% palladium/barium sulfate (0.125 grams) in methanol (30 ml) at room temperature at 45 psi for 3 hours. The reaction was filtered through a pad of Celite and the filtrate concentrated in vacuo to give 0.216 grams of 3-(4-Phenoxyphenylsulfonyl)-7-oxabicyclo[2.2.1]heptane-2-carboxylic acid.

(d) Added the o-benzylhydroxylamine·hydrochloric acid (0.28 grams, 1.73 mmol) to the 3-(4-phenoxyphenylsulfonyl)-7-oxabicyclo[2.2.1]heptane-2-carboxylic acid (0.216 grams, 0.58 mmol) dissolved in CHCl$_3$ with heating to dissolve it. Then the 4-dimethylaminopyridine (0.22 grams, 1.79 mmol) was added and the mixture stirred until complete discussion occurred approximately 5 minutes. Then the 1,3-dicyclohexylcarbodiimide (0.18 grams, 0.87 mmol) was added. After 18 hours stirring at room temperature the reaction was concentrated in vacuo to give 1.05 grams of crude product. Flash chromatography (40% EtOAc/hexane/2%/HOAc/0.5% methanol) gave 0.32 grams of impure product. Flash chromatography (40% EtOAc/hexane) gave 0.212 grams (75%) of pure 3-(4-Phenoxyphenylsulfonyl)-7-oxabicyclo[2.2.1]heptane-2-carboxylicacid benzyloxy amide as a snow white foamy solid.

(e) Combined 3-(4-phenoxyphenylsulfonyl)-7-oxabicyclo[2.2.1]heptane-2-carboxylic acid (0.21 grams, 0.438 mmol) 5% palladium/barium sulfate (0.11 grams) in methanol (20 ml) and hydrogenated on a Parr Shaker at room temperature at 45 psi for 1 ¾ hours. The reaction mixture was filtered and concentrated in vacuo to give 0.175 grams of 3-(4-Phenoxyphenylsulfonyl-7-oxabicyclo[2.2.1]heptane-2-carboxylic acid hydroxyamide as a snow shite foamy solid, m.p. 88.9°–92.9° C. $^1$H-NMR (CD$_3$OD) δ 2.5–2.7 (2H, m), 2.7–2.9 (2H, m), 3.11 (1H, t), 3.84 (1H, d), 4.64 (1H, t), 4.94 (1H, d), 7.10 (4H, d), 7.23 (1H, t), 7.44 (2, t), 7.82 (2H, d); mass spec M$^+$NH$_4^+$ 407. HRMS M$^+$+H$^+$, Calc'd: 390.1011, Found: 390.1022.

We claim:

1. A compound of the formula

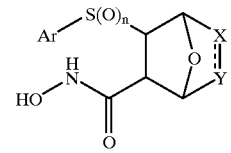

I or a pharmaceutically acceptable salt thereof, wherein the broken line represents an optional double bond;

n is 0, 1 and 2;

X and Y are each independently CR$^1$ wherein R$^1$ is hydrogen, (C$_1$–C$_6$)alkyl optionally substituted by (C$_1$–C$_6$)alkylamino, (C$_1$–C$_6$)alkylthio, (C$_1$–C$_6$)alkoxy, trifluoromethyl, (C$_6$–C$_{10}$)aryl, (C$_5$–C$_9$)heteroaryl, (C$_6$–C$_{10}$)arylamino, (C$_6$–C$_{10}$)arylthio, (C$_6$–C$_{10}$)aryloxy, (C$_5$–C$_9$)heteroarylamino, (C$_5$–C$_9$)heteroarylthio, (C$_5$–C$_9$)heteroaryloxy, (C$_6$–C$_{10}$)aryl(C$_6$–C$_{10}$)aryl, (C$_3$–C$_6$)cycloalkyl, hydroxy(C$_1$–C$_6$)alkyl, (C$_1$–C$_6$)alkyl(hydroxymethylene),piperazinyl, (C$_6$–C$_{10}$)aryl(C$_1$–C$_6$)alkoxy,(C$_5$–C$_9$)heteroaryl (C$_1$–C$_6$)alkoxy, (C$_1$–C$_6$)acylamino, (C$_1$–C$_6$)acylthio, (C$_1$–C$_6$)acyloxy, (C$_1$–C$_6$)alkylsulfinyl, (C$_6$–C$_{10}$)arylsulfinyl, (C$_1$–C$_6$)alkylsulfonyl, (C$_6$–C$_{10}$)arylsulfonyl, amino, (C$_1$–C$_6$)alkylamino or ((C$_1$–C$_6$)alkyl)$_2$amino or R$^1$ is; trifluoromethyl, (C$_1$–C$_6$)alkyl (difluoromethylene), (C$_1$C$_3$)alkyl(difluoromethylene) (C$_1$–C$_3$)alkyl, (C$_6$–C$_{10}$) aryl, (C$_5$–C$_9$)heteroaryl, (C$_3$–C$_6$)cycloalkyl, (C$_1$–C$_6$)alkyl-(hydroxymethylene), R$^3$(C$_1$–C$_6$)alkyl wherein R$^3$ is (C$_1$–C$_6$)acylpiperazino, (C$_6$–C$_{10}$)arylpiperazino, (C$_5$–C$_9$)heteroarylpiperazino, (C$_1$–C$_6$)alkylpiperazino, (C$_6$–C$_{10}$)aryl(C$_1$–C$_6$) alkylpiperazino, (C$_5$–C$_9$)heteroaryl(C$_1$–C$_6$) alkylpiperazino, morpholino, thiomorpholino, pyrrolidino, piperidyl, (C$_1$–C$_6$)alkylpiperidyl, (C$_6$–C$_{10}$)arylpiperidyl, (C$_5$–C$_9$)heteroarylpiperidyl, (C$_1$–C$_6$)alkylpiperidyl(C$_1$–C$_6$)alkyl, (C$_6$–C$_{10}$) arylpiperidyl(C$_1$–C$_6$)alkyl, (C$_5$–C$_9$)heteroarylpiperidyl (C$_1$–C$_6$)alkyl or (C$_1$–C$_6$)acylpiperidyl;

or a group of the formula

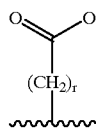

wherein r is 0 to 6;

D is hydroxy, $(C_1-C_6)$alkoxy,piperidyl,$(C_1-C_6)$ alkylpiperidyl,$(C_6-C_{10})$arylpiperidyl, $(C_5-C_9)$ heteroarylpiperidyl, $(C_1-C_6)$acylpiperidyl or $NR^4R^5$ wherein $R^4$ and $R^5$ are each independently selected from the group consisting of hydrogen, $(C_1-C_6)$alkyl optionally substituted by $(C_1-C_6)$alkylpiperidyl, $(C_6-C_{10})$arylpiperidyl, $(C_5-C_9)$heteroarylpiperidyl, $(C_6-C_{10})$aryl, $(C_5-C_9)$heteroaryl, $(C_6-C_{10})$aryl $(C_6-C_{10})$aryl or $(C_3-C_6)$cycloalkyl; or $R^4$ and $R^5$ are each independent by selected from the group consisting of $(C_6-C_{10})$aryl $(C_5-C_9)$heteroaryl, $(C_6-C_{10})$aryl $(C_6-C_{10})$aryl, $(C_3-C_6)$cycloalkyl, $R^6(C_2-C_6)$alkyl, $(C_1-C_5)$alkyl$(CHR^6)(C_1-C_6)$alkyl wherein $R^4$ is hydroxy, $(C_1-C_6)$acyloxy, $(C_1-C_6)$alkoxy, piperazino, $(C_1-C_6)$acylamino, $(C_1-C_6)$alkylthio, $(C_6-C_{10})$ arylthio, $(C_1-C_6)$alkylsulfinyl, $(C_6-C_{10})$arylsulfinyl, $(C_1-C_6)$alkylsufonyl, $(C_6-C_{10})$arylsulfonyl, amino, $(C_1-C_6)$alkylamino, $((C_1-C_6)$alkyl$)_2$amino, $(C_1-C_6)$ acylpiperazino, $(C_1-C_6)$alkylpiperazino, $(C_6-C_{10})$aryl $(C_1-C_6)$alkylpiperazino,$(C_5-C_9)$heteroaryl$(C_1-C_9)$ heteroaryl$(C_1-C_6)$alkylpiperazino,morpholino, thiomorpholino, piperidino or pyrrolidino; or $R^4$ and $R^5$ are each independently selected from the group consisting of $R^7(C_1-C_6)$alkyl, $(C_1-C_6)$alkyl$(CHR^7)$ $(C_1-C_6)$alkyl wherein $R^7$ is piperidyl or $(C_1-C_6)$ alkylpiperidyl; or $R^4$ and $R^5$ is and $CH(R^8)COR^9$ wherein $R^8$ is hydrogen, $(C_1-C_6)$alkyl, $(C_6-C_{10})$aryl $(C_1-C_6)$alkyl, $(C_5-C_9)$heteroaryl$(C_1-C_6)$alkyl, $(C_1-C_6)$alkylthio$(C_1-C_6)$alkyl, $(C_6-C_{10})$arylthio $(C_1-C_6)$alkyl, $(C_1-C_6)$alkylsulfinyl$(C_1-C_6)$alkyl, $(C_6-C_{10})$arylsulfinyl$(C_1-C_6)$alkyl, $(C_1-C_6)$ alkylsulfonyl$(C_1-C_6)$alkyl, $(C_6-C_{10})$arylsulfonyl $(C_1-C_6)$alkyl, hydroxy$(C_1-C_6)$alkyl, amino$(C_1-C_6)$ alkyl, $(C_1-C_6)$alkylamino$(C_1-C_6)$alkyl, $((C_1-C_6)$ alkylamino$)_2(C_1-C_6)$alkyl, $R^{10}R^{11}NCO(C_1-C_6)$alkyl or $R^{10}OCO(C_1-C_6)$alkyl wherein $R^{10}$ and $R^{11}$ are each independently selected from the group consisting of hydrogen, $(C_1-C_6)$alkyl, $(C_6-C_{10})$aryl$(C_1-C_6)$alkyl and $(C_5-C_9)$heteroaryl$(C_1-C_6)$alkyl; and $R^9$ is $R^{12}O$ or $R^{12}R^{13}N$ wherein $R^{12}$ and $R^{13}$ are each independently selected from the group consisting of hydrogen, $(C_1-C_6)$alkyl, $(C_6-C_{10})$aryl$(C_1-C_6)$alkyl and $(C_5-C_9)$ heteroaryl$(C_1-C_6)$alkyl; and Ar is $(C_1-C_6)$alkyl, $(C_6-C_{10})$aryl, $(C_6-C_{10})$aryloxy $(C_6-C_{10})$aryl, $(C_6-C_{10})$aryl$(C_6-C_{10})$aryl, $(C_6-C_{10})$aryl $(C_6-C_{10})$aryl$(C_1-C_6)$alkyl, $(C_6-C_{10})$aryloxy$(C_5-C_9)$ heteroaryl, $(C_5-C_9)$heteroaryl, $(C_1-C_6)$alkyl$(C_6-C_{10})$ aryl, $(C_1-C_6)$alkoxy$(C_6-C_{10})$aryl, $(C_6-C_{10})$aryl $(C_1-C_6)$alkoxy$(C_6-C_{10})$aryl, $(C_6-C_{10})$aryl$(C_1-C_6)$ alkoxy$(C_1-C_6)$alkyl, $(C_5-C_9)$heteroaryloxy$(C_6-C_{10})$ aryl, $(C_1-C_6)$alkyl$(C_5-C_9)$heteroaryl, $(C_1-C_6)$alkoxy $(C_5-C_9)$heteroaryl, $(C_6-C_{10})$aryl$(C_1-C_6)$alkoxy $(C_5-C_9)$heteroaryl, $(C_5-C_9)$heteroaryloxy$(C_5-C_9)$ heteroaryl, $(C_6-C_{10})$aryloxy$(C_1-C_6)$alkyl, $(C_5-C_9)$ heteroaryloxy$(C_1-C_6)$alkyl, $(C_1-C_6)$alkyl$(C_6-C_{10})$ aryloxy$(C_6-C_{10})$aryl, $(C_1-C_6)$alkyl$(C_5-C_9)$ heteroaryloxy$(C_6-C_{10})$aryl, $(C_1-C_6)$alkyl$(C_6-C_{10})$ aryloxy$(C_5-C_9)$heteroaryl, $(C_1-C_6)$alkoxy$(C_6-C_{10})$ aryloxy$(C_6-C_{10})$aryl,$(C_1-C_6)$alkoxy$(C_5-C_9)$ heteroaryloxy$(C_6-C_{10})$aryl or $(C_1-C_6)$alkoxy$(C_6-C_{10})$ aryloxy$(C_5-C_9)$heteroaryl wherein each aryl group is optionally substituted by fluoro, chloro, bromo, $(C_1-C_6)$alkyl, $(C_1-C_6)$alkoxy or perfluoro $(C_1-C_3)$ alkyl.

2. A compound according to claim 1, wherein n is 2.

3. A compound according to claim 1, wherein X and Y are both $CR^1$ wherein $R^1$ is hydrogen.

4. A compound according to claim 1, wherein Ar is $(C_1-C_6)$alkoxy$(C_6-C_{10})$aryl, $(C_6-C_{10})$aryl$(C_1-C_6)$alkoxy $(C_6-C_{10})$aryl, 4-fluorophenoxy$(C_6-C_{10})$aryl, 4-fluorobenzyloxy$(C_6-C_{10})$aryl or $(C_1-C_6)$alkyl$(C_6-C_{10})$ aryloxy$(C_6-C_{10})$aryl.

5. A compound according to claim 1, wherein n is 2, X and Y are both $CR^1$ wherein $R^1$ is hydrogen and Ar is $(C_1-C_6)$ alkoxy$(C_6-C_{10})$aryl, $(C_6-C_{10})$aryl$(C_1-C_6)$alkoxy$(C_6-C_{10})$ aryl, 4-fluorophenoxy$(C_6-C_{10})$aryl, 4-fluorobenzyloxy $(C_6-C_{10})$aryl or $(C_1-C_6)$alkyl$(C_6-C_{10})$aryloxy$(C_6-C_{10})$aryl.

6. A pharmaceutical composition for (a) the treatment of a condition selected from the group consisting of arthritis, cancer, tissue ulceration, macular degeneration, restenosis, periodontal disease, epidermolysis bullosa, sclertitis, in combination with standard NSAID'S and analgesics and in combination with cytotoxic anticancer agents, and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of claim 1 effective in such treatment and a pharmaceutically acceptable carrier.

7. A method for the inhibition of (a) matrix metalloproteinases or (b) the production of tumor necrosis factor (TNF) in a mammal, including a human, comprising administering to said mammal an effective amount of a compound of claim 1.

8. A method for treating a condition selected from the group consisting of arthritis, cancer, tissue ulceration, macular degeneration, restenosis, periodontal disease, epidermolysis bullosa, scleritis, compounds of formula I may be used in combination with standard NSAID'S and analgesics and in combination with cytotoxic anticancer agents, and other diseases characterized by matrix metalloproteinase activity, AIDS, sepsis, septic shock and other diseases involving the production of tumor necrosis factor (TNF) in a mammal, including a human, comprising administering to said mammal an amount of a compound of claim 1, effective in treating such a condition.

* * * * *